United States Patent [19]
Schlichter et al.

[11] Patent Number: 5,819,373
[45] Date of Patent: Oct. 13, 1998

[54] APPARATUS AND METHOD FOR RECOGNIZING AND SEPARATING FOREIGN BODIES FROM FIBER IN A FIBER PROCESSING MACHINE

[75] Inventors: Stefan Schlichter, Viersen; Michael Cieslinski, Unterhaching, both of Germany

[73] Assignee: Trützschler GmbH & Co. KG, Mönchengladbach, Germany

[21] Appl. No.: 642,864

[22] Filed: May 6, 1996

[30] Foreign Application Priority Data

May 5, 1995 [DE] Germany .......................... 195 16 567.5
Oct. 11, 1995 [DE] Germany .......................... 195 37 846.6

[51] Int. Cl.⁶ .............................. D01G 9/00; D01G 23/00
[52] U.S. Cl. .................................. 19/205; 19/0.21; 19/107; 19/65 A; 19/105; 356/335; 406/36; 406/168
[58] Field of Search .................... 19/0.21, 65 R, 19/66 R, 200, 205, 107, 65 A, 105, 97.5, 80 R; 356/238, 237, 335; 406/168, 10, 11, 34, 36

[56] References Cited

U.S. PATENT DOCUMENTS 4,977,645 12/1990 Hösel et al. .
5,125,514 6/1992 Oehler et al. .

FOREIGN PATENT DOCUMENTS

| 0 000 033 | 10/1980 | European Pat. Off. . |
| 0 364 786 | 4/1990 | European Pat. Off. . |
| 0 396 546 | 11/1990 | European Pat. Off. . |
| 0 414 961 | 3/1991 | European Pat. Off. . |
| 0 606 626 | 7/1994 | European Pat. Off. . |
| 483 307 | 9/1929 | Germany . |
| 1 815 700 | 6/1970 | Germany . |
| 31 33 744 | 8/1982 | Germany . |
| 38 25 109 | 2/1990 | Germany . |
| 284 911 | 11/1990 | Germany . |
| 40 18 847 | 12/1991 | Germany . |
| 2 260 145 | 4/1993 | United Kingdom . |
| 89/01832 | 3/1989 | WIPO . |

*Primary Examiner*—Michael A. Neas
*Attorney, Agent, or Firm*—Spencer & Frank

[57] ABSTRACT

An apparatus for detecting a foreign substance in a pneumatically advancing fiber tuft stream and for separating the foreign substance therefrom includes a conduit; an optical sensor arrangement situated at a first location of the conduit for detecting a foreign substance in flight and for emitting signals representing the foreign substance; a separating arrangement situated at a second location of the conduit downstream of the first location as viewed in the conveying direction; an evaluating device for processing the signals; and a control device connected to the optical sensor arrangement, the separating arrangement and the evaluating device for operating the separating arrangement.

14 Claims, 8 Drawing Sheets

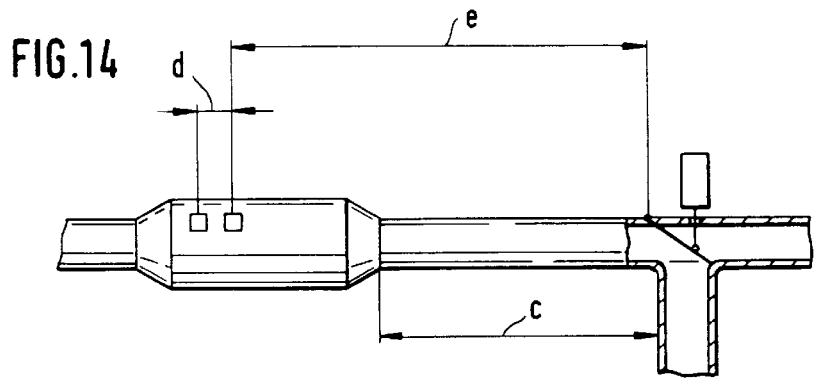
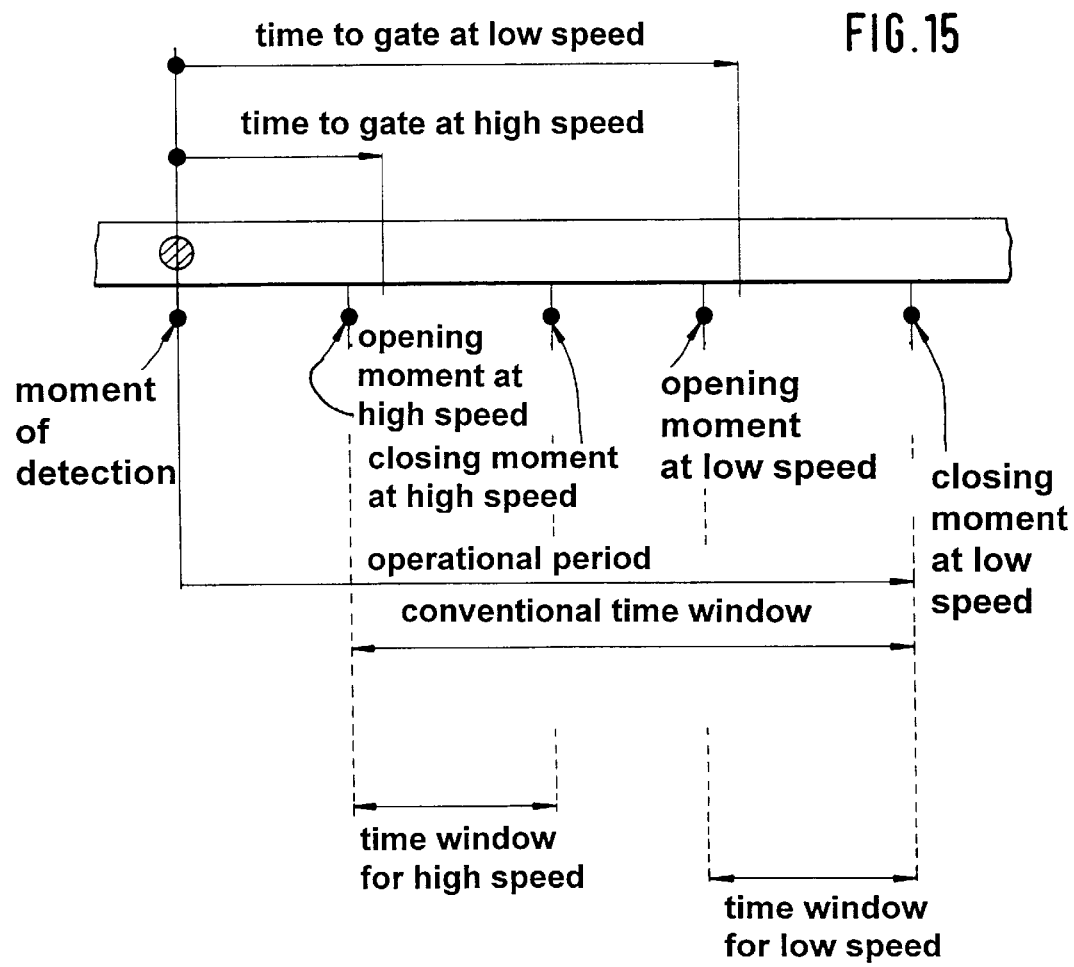

APPARATUS AND METHOD FOR RECOGNIZING AND SEPARATING FOREIGN BODIES FROM FIBER IN A FIBER PROCESSING MACHINE

CROSS REFERENCE TO RELATED APPLICATION

This application claims the priority of German Application Nos. 195 16 567.5 filed May 5, 1995 and 195 37 846.6 filed Oct. 11, 1995.

BACKGROUND OF THE INVENTION

This invention relates to an apparatus which finds application in a fiber preparation (cleaning) line for recognizing and separating foreign substances such as pieces of fabric, straps, strings, pieces of foil present in a fiber tuft mass removed from fiber bales by a bale opener. The apparatus is of the type which includes an optical sensor system for recognizing the foreign substance, followed by a separating device for removing such substance. The optical sensor system is connected with the separating device by means of an evaluating device and a control device.

A known apparatus of the above-outlined type may be installed in a fiber processing (cleaning and blending) line downstream of a coarse cleaning machine or a mixer, that is, prior to introducing the fiber tufts into an apparatus which performs fine cleaning. The fiber tufts are admitted by a suction condenser into a supply duct, one wall of which is formed by an endless, obliquely oriented conveyor belt. Thereafter, the fiber tufts are carried by the conveyor past an optical recognizing system (such as an optical color sensor system). An evaluating device evaluates the measurements and, upon appearance of foreign substances, actuates a corresponding group of nozzles of a nozzle bank. The nozzles of a nozzle group are actuated as soon as the upstream-arranged optical sensor has recognized the foreign substances. The fiber tufts blown out of the system and containing foreign substances are introduced into a waste container. The remaining, uncontaminated good fibers are introduced into a collecting funnel and then reach the consecutive cleaning machine. It is a disadvantage of such a prior art system that it requires substantial technological and constructional outlay.

SUMMARY OF THE INVENTION

It is an object of the invention to provide an improved apparatus of the above-outlined type from which the discussed disadvantages are eliminated and which, in particular, makes possible an improved recognition and separation of foreign substances in a simple manner.

This object and others to become apparent as the specification progresses, are accomplished by the invention, according to which, briefly stated, the apparatus for detecting a foreign substance in a pneumatically advancing fiber tuft stream and for separating the foreign substance therefrom includes a conduit; an optical sensor arrangement situated at a first location of the conduit for detecting a foreign substance in flight and for emitting signals representing the foreign substance; a separating arrangement situated at a second location of the conduit downstream of the first location as viewed in the conveying direction; an evaluating device for processing the signals; and a control device connected to the optical sensor arrangement, the separating arrangement and the evaluating device for operating the separating arrangement.

The apparatus according to the invention makes possible the removal of foreign substances as early as the beginning of the process, for example, immediately downstream of the bale opener and before further handling of the fiber tufts, for example, by a condenser. By virtue of the fact that the fiber material is not presented on a separate conveyor such as a conveyor belt but in an air stream, a very significant structural simplification is achieved. By means of the apparatus according to the invention the following exemplary types of foreign substances may be reliably recognized and separated: plastic sheet parts, pieces of fabric made of plastic films, jute or cotton, meshed pieces, plastic, jute or cotton strings, pieces of colored polypropylene sheets or the like, oily fiber tufts and also pieces having a higher specific weight, such as pebbles, seeds and the like. As a result, operational disturbances during further processing of the fiber tufts, for example, wear of clothing, malfunctions in the machinery, thread breakages, interference with the coloring and the like are significantly reduced.

BRIEF DESCRIPTION OF THE DRAWINGS

FIG. 14 is a schematic side elevational view of the apparatus according to FIG. 2 illustrating distances for determining conveying times.

FIG. 15 is a diagram illustrating delays between recognition and elimination of foreign substances.

DESCRIPTION OF THE PREFERRED EMBODIMENTS

Figure 1:
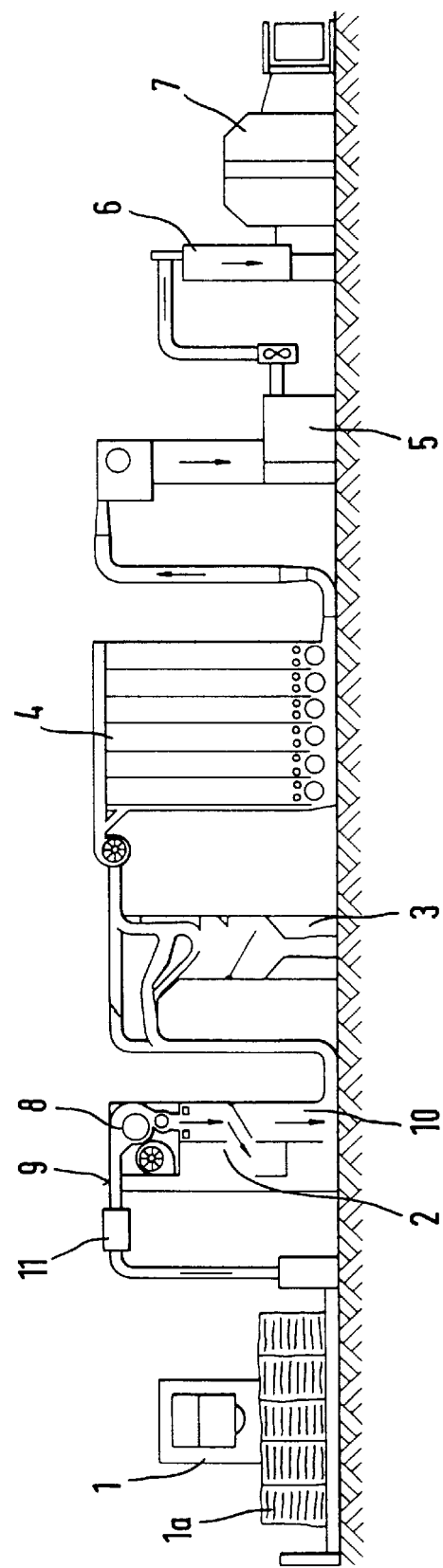
FIG. 1 is a schematic side elevational view of a fiber tuft processing line including the apparatus according to the invention.

FIG. 1 shows a fiber tuft processing (opening, cleaning and mixing) line formed of a plurality of machines connected in series by pneumatic fiber-transporting ducts, such as duct 9 in which the fiber-conveying air stream is generated by transport fans. The processing line includes a bale opener 1 and a multi-mixer 4 between which an apparatus 2 for recognizing and separating metal substances and a heavy particle separator are arranged. The inlet zone of the machine 2 includes a condenser 8. Downstream of the multi-mixer 4 a fine opener 5, a card feeder 6 and a carding machine 7 are arranged. The fiber tuft processing line formed of components 1–5 may supply a plurality of carding machines 7, each provided with its own card feeder 6. The fiber bales worked on by the bale opener 1 are designated at 1*a*. An apparatus 11 structured according to the invention is inserted in the duct 9 immediately downstream of the bale opener 1 at the duct input end where the fiber tufts are received from the bale opener 1.

Figure 2:
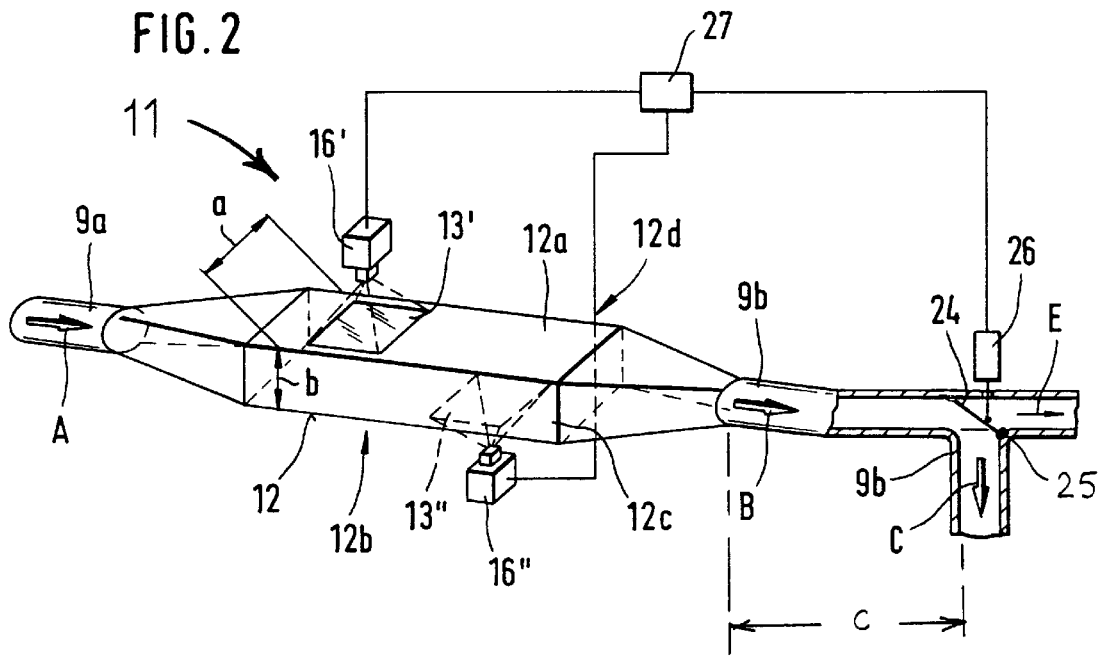
FIG. 2 is a schematic perspective view of a preferred embodiment of the invention.

Turning to FIG. 2, the apparatus 11 includes a conduit 12 which is inserted between tubular parts 9*a* and 9*b* of the tuft-transporting duct 9. The conduit 12 has a rectangular cross section having, for example, a width a=600–800 mm and a height b=100–200 mm. In the upper wall 12*a* and 12*b* of the conduit 12 respective windows 13' and 13" of light-transparent material (such as glass or plastic) are provided. Cameras 16' and 16" (such as diode-line cameras) are supported in an orientation towards the windows 13', 13" to observe the inner space of the conduit 12 in which an air stream conveys fiber tufts in the direction A at high speed. The camera 16" is situated at a distance downstream of the camera 16' as viewed in the direction of fiber tuft flow in the conduit 12. The downstream end of the conduit 12 is connected by means of a coupling element to the cross-sectionally circular tubular part 9*b* which, at a spacing c from its beginning, is bent downwardly at 90°. At the bend the duct part 9*b* is provided with a separating gate 24 which is articulated to the duct part 9*b* at 25 and which may be pivoted by means of a setting device, such as a pneumatic cylinder 26. The setting device 26 is coupled to the cameras 16' and 16" with the intermediary of an electronic control and regulating device 27. In FIG. 2 the separating gate 24 is shown in its position it assumes for the normal tuft-conveying operation. Upon recognition of a foreign substance by the cameras 16', 16" the gate 24 is pivoted after a predetermined delay by the actuating device 26 as commanded by the control device 27 to close the duct part 9*b* and open the flow path toward a non-illustrated waste chamber into which the detected foreign substance E is admitted.

Figure 3:
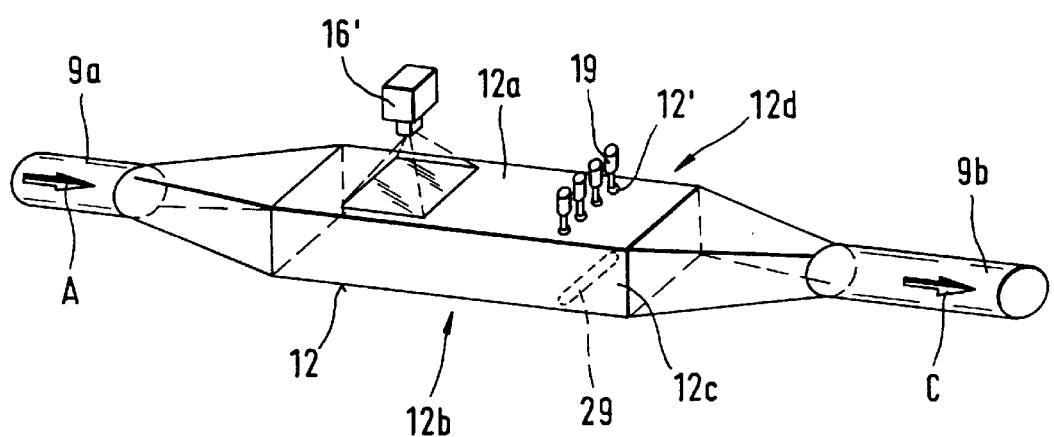
FIG. 3 is a perspective view of a variant of FIG. 2.

In FIG. 3, downstream of the camera 16', there are provided a row of blow nozzles 19 which direct their air stream into the conduit 12 through apertures 12' provided in the top wall 12*a* of the conduit 12 substantially over its entire width. In the bottom wall 12*b* of the conduit 12, in alignment with the nozzles 19, an opening 29 is provided through which the foreign substances may be blown out by the nozzles 19. As will be described later, measures are provided for maintaining the conveying air flow in the conduit 12 at the proper pressure despite the pneumatic (nozzle-blown) removal of foreign substances.

Figure 4:
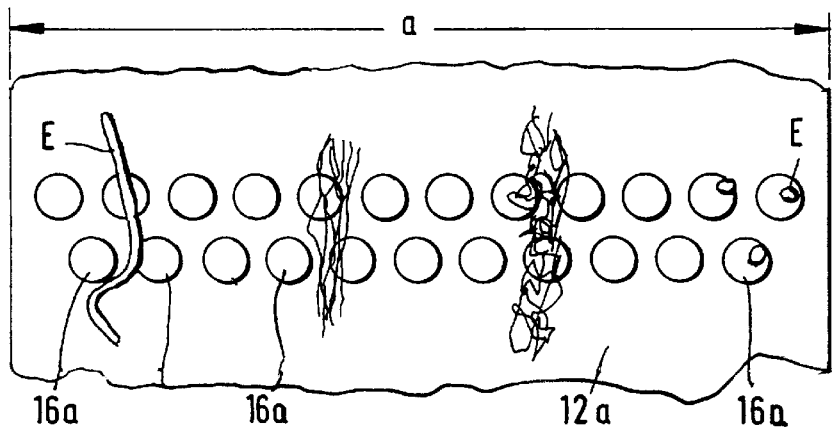
FIG. 4 is a schematic top plan view of a sensor system including a plurality of sensors according to the invention.

According to the embodiment shown in FIG. 4, instead of cameras 16' and 16" an optical sensor system is provided which is formed of a plurality of sensor elements 16*a* (for example, color sensors) arranged in two parallel rows at the upper conduit wall 12*a* along the width a of the conduit 12 such that the sensor elements 16*a* of one row are staggered with those forming the other row.

Figure 5:
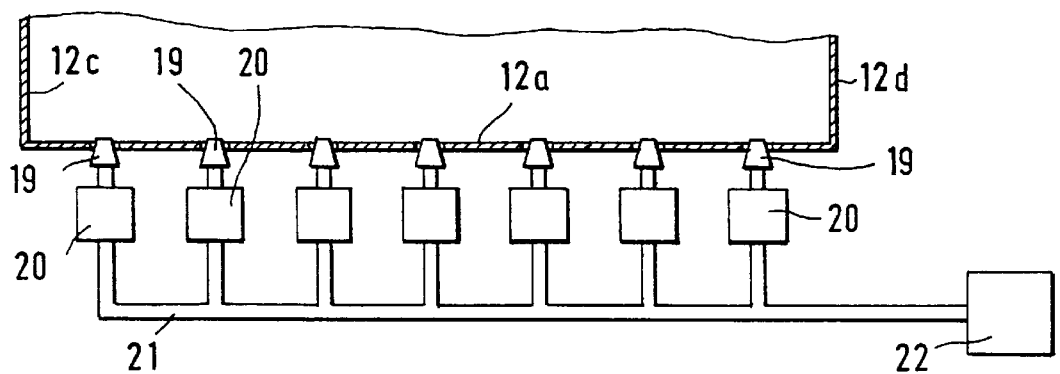
FIG. 5 is schematic front elevational view of a pneumatic blowout device including a series of blow nozzles according to the invention.

Turning to FIG. 5, a plurality of blow nozzles 19 are shown in a row extending along the width of the conduit 12 and arranged at the top wall 12*a* as shown in the perspective illustration of FIG. 3. Each blow nozzle 19 is associated with a respective valve 20 coupled to a common pneumatic line 21 which, in turn, is connected with a pneumatic pressure source 22. It is to be understood that the optical sensor system 16 such as the sensors 16*a* or the cameras 16', 16" as well as the row of nozzles 19 may be arranged in the vertical side walls 12*c*, 12*d* of the conduit 12.

Figure 6:
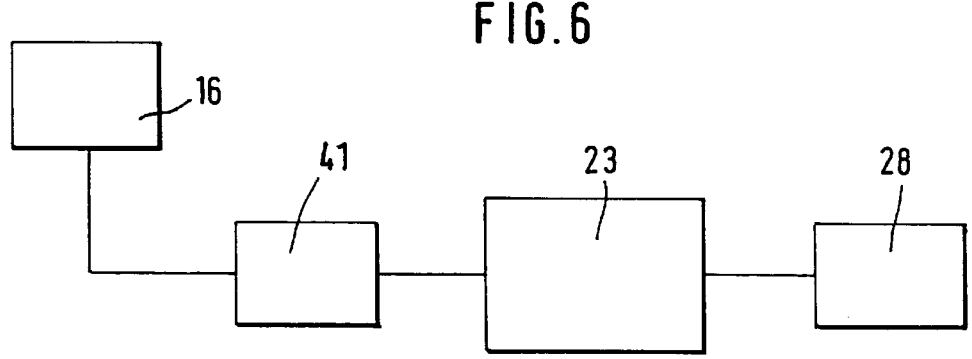
FIG. 6 is a block diagram of an electronic control of sensors and blow nozzles.

As shown in FIG. 6, the optical sensor system 16 (formed of one or more cameras 16' and/or 16" or sensor elements 16*a*), an image processing device 41 and a valve control 28 for the valves 20 are connected to the electronic control and regulating device 23.

Figure 7:
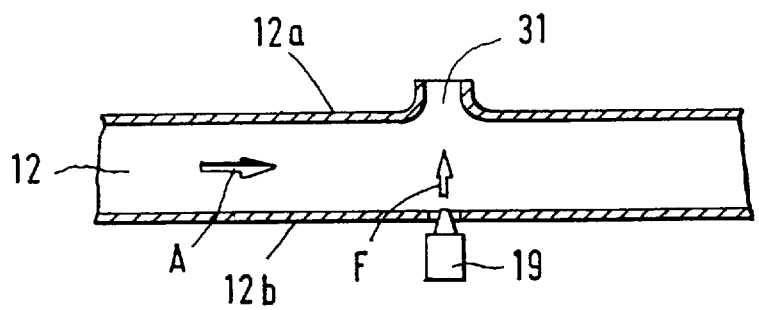
FIG. 7 is a schematic side elevational view of the structure shown in FIG. 5.

According to FIG. 7, the nozzles 19 (only one is visible) are arranged at the bottom wall 12*b* of the conduit 12 and, when actuated, emit an air stream F to separate the detected foreign substances from the fiber tuft stream flowing in the conduit 12 in the direction A and eject such foreign substances through a discharge opening 31 provided in the top conduit wall 12*a* in alignment with the row of the nozzles 19.

Figure 8:
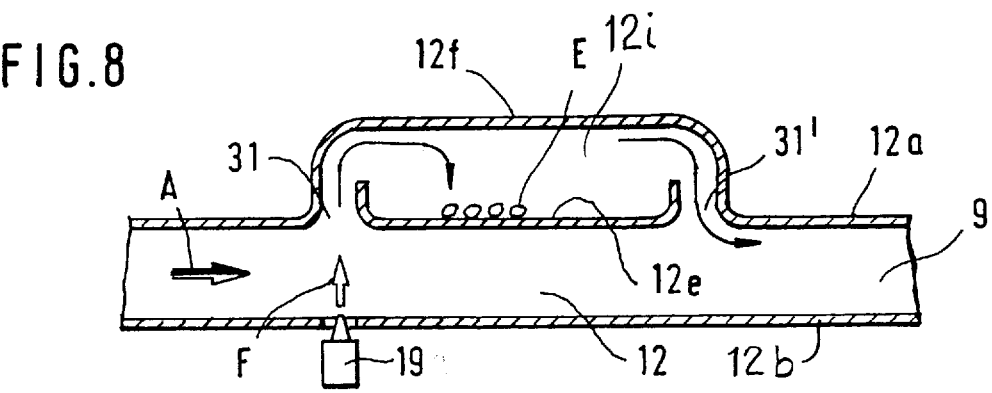
FIG. 8 is a schematic side elevational view of a variant of FIG. 7.

In the arrangement according to FIG. 8, the foreign substances are blown by the air stream F through the opening 31 into a waste chamber 12*i* formed at the top wall 12*a* by a wall portion 12*f* and a wall portion 12*e*. The foreign substances E fall on the bottom of the chamber 12*i* by gravity, while the separating air stream F exits therefrom through a return opening 31' to rejoin the conveying stream in the conduit 12 at a location downstream of the inlet opening 31.

Figure 9:
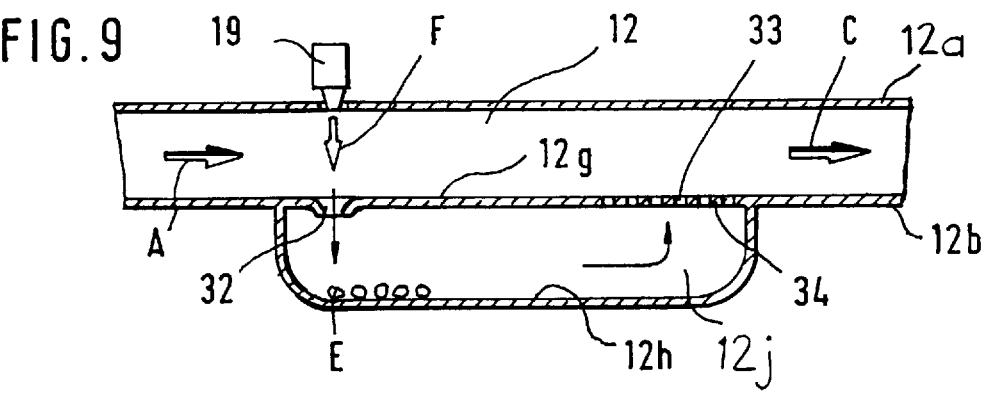
FIG. 9 is a schematic side elevational view of a variant of FIG. 8.

The arrangement shown in FIG. 9 is similar to that illustrated in FIG. 8 except that the row of nozzles 19 is arranged at the top wall 12*a* and the air stream F is directed downwardly and enters through an inlet opening 32 into a waste chamber 12*j* formed by wall portions 12*h* and 12*g*. The air stream, after the foreign bodies E have been deposited in the chamber 12*j*, return into the conduit 12 through an outlet opening 33 which is provided with a screen (sieve) 34.

Figure 10:
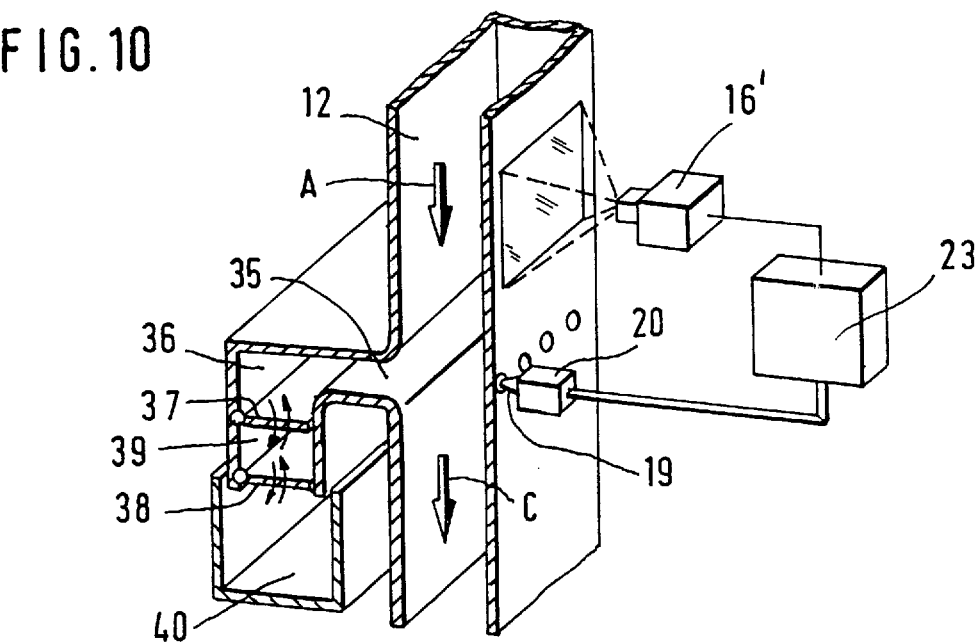
FIG. 10 is a schematic sectional perspective view of a preferred embodiment.

In the construction according to FIG. 10 the conduit 12 is oriented vertically, and the blow nozzles 19 are arranged at a vertical wall of the conduit 12, underneath the camera 16'. The opening 35 which is aligned with the row of nozzles 19 (of which only one is shown for the sake of clarity) is adjoined by a foreign substance removal device 35 such as a separating chamber, an air exit duct or the like. The conduit 36 is oriented vertically downwardly at 90° from the opening 36 and thus extends parallel to the conduit 12. The outlet of the removal device 36 is controlled by an air lock 39 formed of two rotatable gates 37 and 38 which are expediently sequentially operated to maintain the conduit 12 airtight. Underneath the outlet of the removal device 36 a container 40 is disposed for receiving the foreign substances E.

Figure 11:
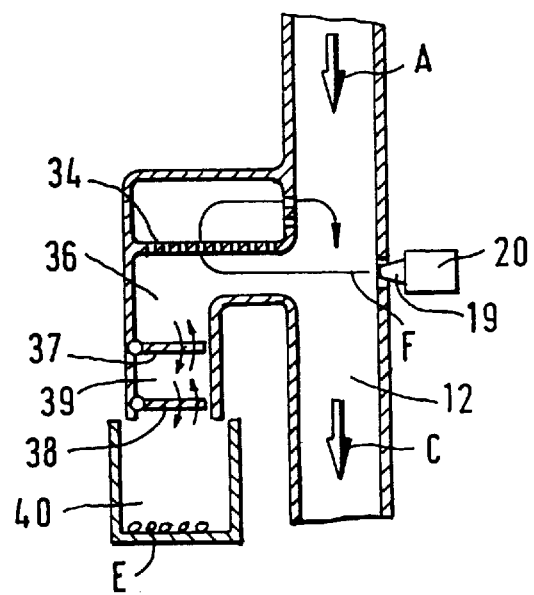
FIG. 11 is a schematic sectional side elevational view of a variant of the structure shown in FIG. 10.

The construction illustrated in FIG. 11 differs from that shown in FIG. 10 essentially only in that the compressed air F emitted by the nozzle 19 is reintroduced into the conduit 12 after the foreign substances have fallen towards the gates 37, 38 by gravity. The air stream F flows through a sieve 34 which is situated above the removal device 36.

Figure 12:
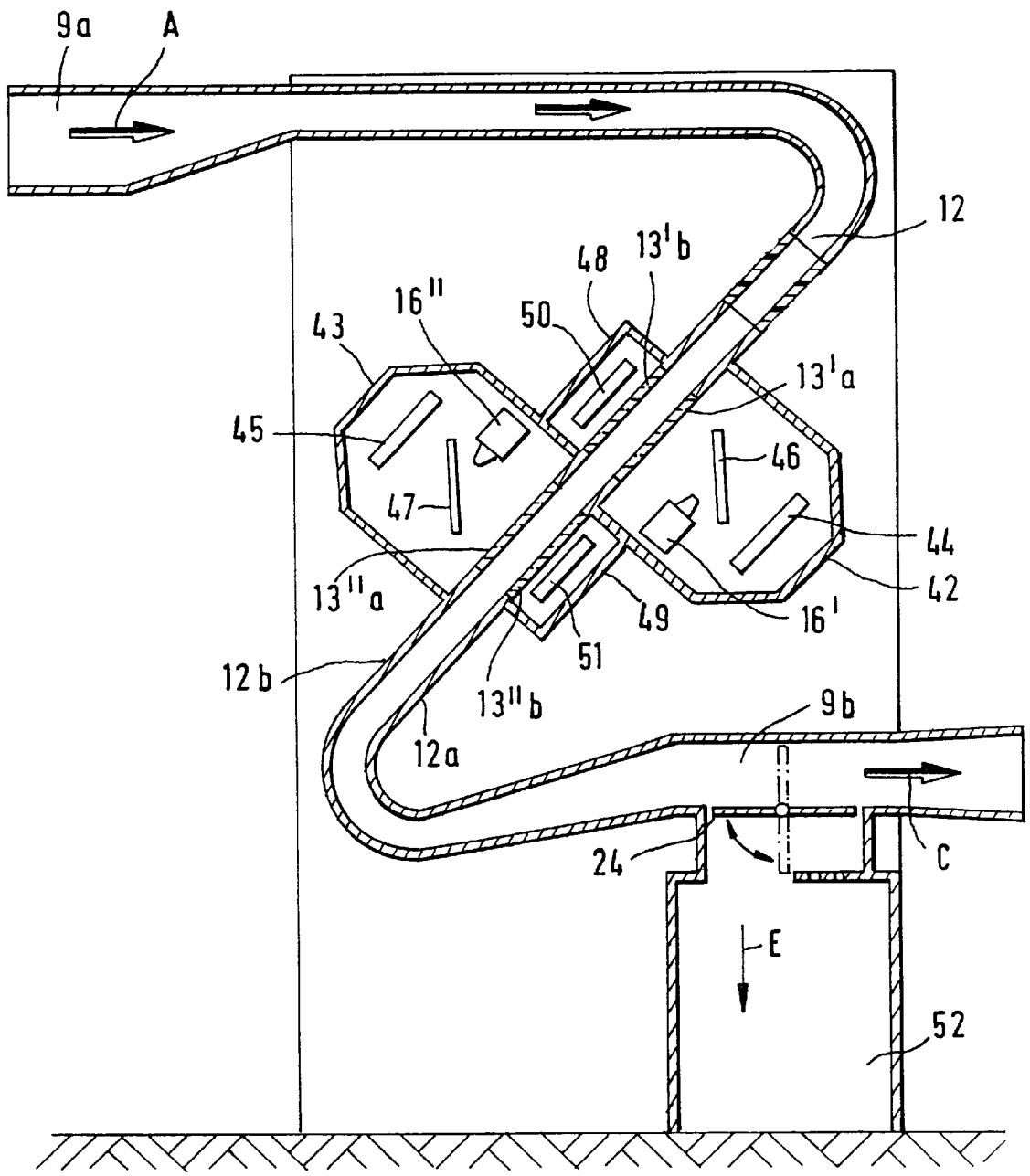
FIG. 12 is a schematic side elevational view of a further preferred embodiment of the invention.

Turning to the embodiment illustrated in FIG. 12, to the exterior of the conduit 12 two housings 42 and 43 are attached in which respective cameras 16', 16" as well as respective illuminating devices 44 and 45 are arranged. Further, in the housings 42, 43 respective mirrors 46, 47 are disposed at such an angle that an optical axis from the cameras 16', 16" through the respective windows 13'*a*, 13"*a* to the interior of the conduit 12 is maintained. The illuminating devices 44, 45 emit a light beam through the windows 13'*a* and 13"*a* into the inner space of the conduit 12. On the side opposite the housings 42, 43 two further housings 48 and 49 are attached to the exterior of the conduit 12 for receiving illuminating devices 50, 51 emitting respective light beams through the windows 13'*b*, 13"*b* into the conduit 12. The housings 42, 48 and the housing 43, 49 are arranged offset relative to one another as viewed in the direction of air flow in the conduit 12. It is further seen that the camera 16' detects light from the illuminating source 44 reflected by the material flow in the conduit 12, while the camera 16' detects light from the illuminating source 50 transmitted by the material flow in the conduit 12. Likewise, the camera 16" detects light from the illuminating source 45 reflected by the material flow in the conduit 12, while the camera 16" detects light from the illuminating source 51 transmitted by the material flow in the conduit 12.

The apparatus according to the invention makes possible the recognition of foreign substances in a stream of cotton tufts. In particular, the following are recognized:

Non-transparent pieces, for example, wood, stones, metal, strings, paper, etc;

Parts having a color which is foreign to the fiber coloring, such as dirt, leaves, etc; and Sparkling parts, such as pieces of foil or thin sheets.

The cameras 16', 16" detect the fiber tufts through the windows 13'*a*, 13'*b*; 13"*a*, 13"*b* as they fly past. This procedure is effected by the combination of transmitted light and reflected light generated by the illuminating devices 44 and 50 for the camera 16' and by the illuminating devices 45 and 51 for the camera 16". The evaluation is based on the principle of a desired value/actual value comparison. As a desired parameter, the reflection intensity related to the transmitted beam intensity is utilized. The characteristic of the fiber material, such as cotton is determined by the system automatically and utilized as a reference. Substances having differing characteristics are recognized when a dimension is, for example, 5 mm along the smallest axis. Such a foreign substance is thereafter removed from the fiber tuft stream by setting the gate 24 into a position in which the conveyed material, containing the foreign substance E, is temporarily deflected into a waste container 52.

The reflected light module accommodated in the housing 42 includes a semiconductor flashlight device 44 having a high homogeneity, a command-controlled high-speed measuring camera 16' with digital data output (such as disclosed, for example, in German Offenlegungsschrift 43 13 621) and a deflecting mirror 46 which contributes to the reduction of the structural height. The transmitted light module accommodated in the housing 48 includes a large-area semiconductor flashlight device 50 having a high intensity. The reflected and transmitted light modules contained in the housings 43 and 49 and including the camera 16" have corresponding structural elements and devices.

In operation, two pictures are taken in rapid succession of the material flow, once by transmitted light and once by reflected light. The two pictures are combined and evaluated together. The light flashes are controlled by the cameras or by their control. Light of different wavelengths may be used for the individual takes. It is also feasible to utilize more than one illuminating device 44, 48; 45, 49 for one take. For example, the reflected light module in the housing 42 may have more than one illuminating device 44. The illumination may be effected from different directions or different sides. Also, for the illumination, light sources with different wavelength may be used. Also, the different directions, sides and wavelengths may be combined with one another and different exposure times may be set.

Figure 13:
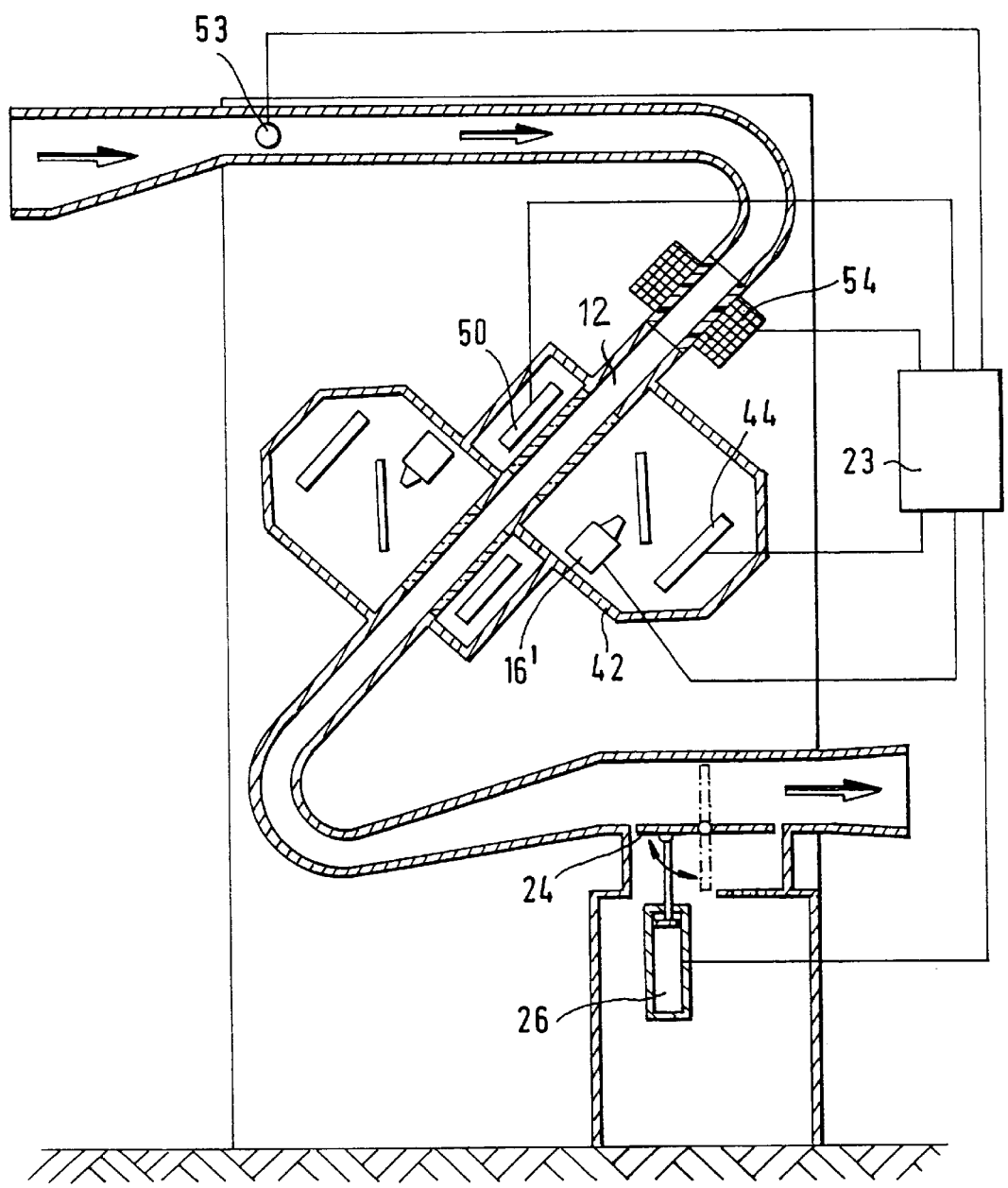
FIG. 13 is a view similar to FIG. 12 including a block diagram showing an electronic control and regulating device.

In the embodiment illustrated in FIG. 13 the FIG. 12 construction is complemented with a fire and spark sensor 53 and a metal detector 54 associated with the conduit 12. Such sensors are described, for example, in German Offenlegungsschriften 41 31 188 and 41 29 882, respectively. The fire and spark detector 53, the metal detector 54, the camera 16' (or, if required, the camera 16"), the illuminating devices 44, 50 (and, if required, the illuminating devices 45, 51) and the hydraulic cylinder 26 for operating the gate 24 are connected with the electronic control and regulating device 23.

For a reliable operation of the apparatus, the cameras 16' and 16" have to be arranged at a sufficient distance from the separating gate 24 (or nozzles 19, if a pneumatic removal of foreign substances is utilized). If such a distance is too short, the foreign substances may have already passed the gate 24 before switching it to a position in which material is deviated into the waste container. Tests have shown that the period that elapses from the moment of detecting a foreign substance until the gate 24 is switched is 0.2 seconds. At a speed of 10 m/s of the fiber/air mixture in the conduit 12 the distance of the cameras 16', 16" from the gate 24 should thus be greater than 2 m. Considering an appropriate safety factor, a distance of 3 m has been found to be advantageous. Since, in particular, larger tufts having a lower speed than the fiber/air mixture may pass through the conduit 12, it has to be ensured that the gate 24 is not prematurely reset from its waste-discharging position, otherwise the foreign substance may pass by the gate 24 when it has already been reset and is thus conveyed normally with the material rather than being separated. Tests have shown that for a fiber/air mixture speed of 10 m/sec in the conduit 12 and for a distance of 3 m between the cameras 16', 16" on the one hand and the gate 24 on the other hand, a dwell period of 1 second of the gate 24 in its deviating position is sufficient to safely separate every foreign substance detected by the apparatus. Such a period may be set in the control part of the cameras 16', 16" and may be changed if other conveying speeds are used in the conduit 12.

As noted before, two pictures are taken of the same object in a short sequence. From the distance of the detected substance in the picture and from the time difference between the two takes the speed of the foreign substance is determined. From the obtained speed, in turn, the time is calculated which is required for the substance to reach the separating gate 24. The time period determined in this manner is applied to the control device 23 and is utilized for opening the gate 24 for separating the detected object. In this manner, a reduction of the separated quantities (particularly good fibers) is possible because the time window of the open period of the gate 24 may be reduced. Since the objects have different speeds in the tuft stream, in the absence of such determination a large time window must be present to ensure that both the fastest and the slowest foreign particles are separated.

First, according to FIG. 14, the transport velocity $v_1$ of the foreign substance is determined in the zone of the camera:

$$v_1 = \frac{d}{t_1}, \text{wherein}$$

$v_1$=the conveying speed of the detected object d=the distance between two images of the substance $t_1$=the transporting period for the distance d.

Thereafter the transporting period $t_2$ of the object from the camera 16' to the gate 24 is determined:

, wherein $$t_2 = \frac{e}{v_1}$$

$t_2$=transporting period for the path e
e=distance between the second image and the separating gate 24
$v_1$=the transporting speed of the photographed object.

The time period $t_2$ measured in this manner is used for activating and deactivating the hydraulic cylinder 26 operating the separating gate 24, as shown in FIGS. 2 and 13.

It will be understood that the above description of the present invention is susceptible to various modifications, changes and adaptations, and the same are intended to be comprehended within the meaning and range of equivalents of the appended claims.

It is claimed:

1. An apparatus for detecting a foreign substance in a fiber tuft stream and for separating the foreign substance therefrom, comprising
    (a) a conduit having a discharge opening;
    (b) means for generating an airstream for pneumatically advancing fiber tufts through said conduit in a conveying direction;
    (c) optical sensor means situated at a first location of said conduit for detecting a foreign substance in flight and for emitting signals representing said foreign substance;
    (d) separating means situated at a second location of said conduit downstream of said first location as viewed in the conveying direction; said separating means comprising nozzle means for directing an air stream into said interior transversely to said conveying direction to blow the foreign substance out of the fiber stream; said nozzle means comprising a plurality of blow nozzles arranged in a row at said conduit; said row extending transversely to said conveying direction; said discharge opening of said conduit being aligned with said blow nozzles; the air stream emitted by said blow nozzles exiting from said interior through said discharge opening;
    (e) evaluating means for processing said signals;
    (f) control means connected to said optical sensor means, said separating means and said evaluating means for operating said separating means;
    (g) a receptacle attached laterally to said conduit; said discharge opening maintaining communication between said receptacle and said interior of said conduit; and
    (h) a return opening in said receptacle for maintaining communication between said receptacle and said interior of said conduit; said return opening being situated downstream of said discharge opening as viewed in said conveying direction; said airstream entering said discharge opening, depositing the foreign substance in said receptacle and rejoining said interior through said return opening.

2. The apparatus as defined in claim 1, further comprising a filtering screen situated across said return opening.

3. An apparatus for detecting a foreign substance in a fiber tuft stream and for separating the foreign substance therefrom, comprising
    (a) a conduit having an interior;
    (b) means for generating an airstream for pneumatically advancing fiber tufts through said conduit in a conveying direction;
    (c) optical sensor means situated at a first location of said conduit for detecting a foreign substance in flight and for emitting signals representing said foreign substance; said optical sensor means including a plurality of sensor elements arranged in a row in a side-by-side relationship along substantially an entire width of said interior measured perpendicularly to said conveying direction;
    (d) separating means situated at a second location of said conduit downstream of said first location as viewed in the conveying direction;
    (e) evaluating means for processing said signals; and
    (f) control means connected to said optical sensor means, said separating means and said evaluating means for operating said separating means.

4. An apparatus for detecting a foreign substance in a fiber tuft stream and for separating the foreign substance therefrom, comprising
    (a) a conduit having an interior;
    (b) means for generating an airstream for pneumatically advancing fiber tufts through said conduit in a conveying direction;
    (c) optical sensor means situated at a first location of said conduit for detecting a foreign substance in flight and for emitting signals representing said foreign substance; said optical sensor means including a plurality of sensor elements being arranged in a plurality of parallel rows; in each said row said sensor elements being in a side-by-side relationship along substantially an entire width of said interior measured perpendicularly to said conveying direction; the sensor elements of one of said rows being staggered relative to the sensor elements of an adjoining said row;
    (d) separating means situated at a second location of said conduit downstream of said first location as viewed in the conveying direction;
    (e) evaluating means for processing said signals; and
    (f) control means connected to said optical sensor means, said separating means and said evaluating means for operating said separating means.

5. An apparatus for detecting a foreign substance in a fiber tuft stream and for separating the foreign substance therefrom, comprising
    (a) a conduit having a discharge opening;
    (b) means for generating an airstream for pneumatically advancing fiber tufts through said conduit in a conveying direction;
    (c) optical sensor means situated at a first location of said conduit for detecting a foreign substance in flight and for emitting signals representing said foreign substance;
    (d) separating means situated at a second location of said conduit downstream of said first location as viewed in the conveying direction; said separating means comprising nozzle means for directing an air stream into said interior transversely to said conveying direction to blow the foreign substance out of the fiber stream; said nozzle means comprising a plurality of blow nozzles arranged in a row at said conduit; said row extending transversely to said conveying direction; said discharge opening of said conduit being aligned with said blow nozzles; the air stream emitted by said blow nozzles exiting from said interior through said discharge opening;
    (e) evaluating means for processing said signals;

(f) control means connected to said optical sensor means, said separating means and said evaluating means for operating said separating means;

(g) a waste duct having an opening in alignment with said blow nozzles to receive the airstream therefrom; and (h) a dual-gate air lock situated in said waste duct.

6. An apparatus for detecting a foreign substance in a fiber tuft stream and for separating the foreign substance therefrom, comprising (a) a conduit having a discharge opening;

(b) means for generating an airstream for pneumatically advancing fiber tufts through said conduit in a conveying direction;

(c) optical sensor means situated at a first location of said conduit for detecting a foreign substance in flight and for emitting signals representing said foreign substance;

(d) separating means situated at a second location of said conduit downstream of said first location as viewed in the conveying direction; said separating means comprising nozzle means for directing an air stream into said interior transversely to said conveying direction to blow the foreign substance out of the fiber stream; said nozzle means comprising a plurality of blow nozzles arranged in a row at said conduit; said row extending transversely to said conveying direction; said discharge opening of said conduit being aligned with said blow nozzles; the air stream emitted by said blow nozzles exiting from said interior through said discharge opening;

(e) evaluating means for processing said signals;

(f) control means connected to said optical sensor means, said separating means and said evaluating means for operating said separating means;

(g) a waste duct having an opening in alignment with said blow nozzles to receive the airstream therefrom; and (h) recirculating means for returning the airstream from said waste duct into said interior.

7. The apparatus as defined in claim 6, wherein said recirculating means comprises a screen for filtering said airstream prior to returning into said interior.

8. A method of detecting a foreign substance in a fiber tuft stream conveyed pneumatically in a conduit in a conveying direction, comprising the following steps:

(a) detecting the presence of a foreign substance in the fiber tuft stream by an optical sensor arrangement at a first location of the conduit;

(b) determining the velocity of the detected foreign substance in said first location; said step of determining the velocity including
   (1) taking two pictures of the detected foreign substance in rapid succession by said optical sensor arrangement;
   (2) measuring a distance between the two pictures; and
   (3) calculating the velocity of the foreign substance based on said distance and a delay between taking the two pictures; and (c) starting to deflect the fiber tuft stream into a waste-receiving device at a second location of said conduit at a moment determined as a function of said velocity.

9. A fiber tuft processing line having a plurality of fiber tuft processing machines serially connected to one another by a pneumatic duct for pneumatically conveying fiber tufts in a stream from one machine to a successive machine in a conveying direction; said pneumatic duct having an input end upstream of said fiber tuft processing machines as viewed in said conveying direction; said fiber tuft processing line further including an apparatus for detecting a foreign substance in the fiber tuft stream and for separating the foreign substance therefrom; said apparatus being situated in said pneumatic duct downstream of said input end and upstream of said fiber tuft processing machines; said apparatus comprising (a) a conduit forming part of said pneumatic duct for guiding the fiber tuft stream in said conveying direction;

(b) optical sensor means situated at a first location of said conduit for detecting a foreign substance in flight and for emitting signals representing said foreign substance; said first location being situated in said pneumatic duct downstream of said input end and upstream of all of said fiber tuft processing machines of said line;

(c) separating means situated at a second location of said conduit downstream of said first location as viewed in the conveying direction;

(d) evaluating means for processing said signals; and (e) control means connected to said optical sensor means, said separating means and said evaluating means for operating said separating means.

10. The fiber tuft processing line as defined in claim 9, wherein one of said fiber processing machines is a fiber tuft opener situated downstream of said apparatus as viewed in said conveying direction.

11. A method of detecting a foreign substance in a fiber tuft stream, comprising the following steps:

(a) driving the fiber tuft stream through a conduit serially connecting to one another fiber tuft processing machines of a fiber processing line;

(b) detecting the presence of a foreign substance in the fiber tuft stream by an optical sensor arrangement at a first conduit location situated upstream of all the fiber tuft processing machines of the line;

(c) determining the velocity of the detected foreign substance in said first conduit location and (d) starting to deflect the fiber tuft stream into a waste-receiving device at a second conduit location at a moment determined as a function of said velocity.

12. The method as defined in claim 11, further comprising the step of discontinuing to deflect the fiber tuft stream into the waste-receiving device at a moment determined as a function of said velocity.

13. A fiber processing line comprising (a) a fiber bale opener;

(b) a plurality of fiber processing machines;

(c) a pneumatic duct for serially connecting said fiber bale opener to said fiber processing machines and said fiber processing machines to one another for pneumatically conveying fiber tufts in a stream from said fiber bale opener consecutively to said fiber processing machines; and (d) an apparatus for detecting a foreign substance in the fiber tuft stream and for separating the foreign substance therefrom; said apparatus being disposed downstream of said fiber bale opener and upstream of all of said fiber processing machines of said line as viewed in a direction of fiber tuft travel through said fiber processing line; said apparatus comprising (1) a conduit forming part of said pneumatic duct for guiding the fiber tuft stream in a conveying direction;
(2) optical sensor means situated at a first location of said conduit for detecting a foreign substance in flight and for emitting signals representing said foreign substance;
(3) separating means situated at a second location of said conduit downstream of said first location as viewed in the conveying direction;
(4) evaluating means for processing said signals; and
(5) control means connected to said optical sensor means, said separating means and said evaluating means for operating said separating means.

14. The fiber processing line as defined in claim 13, wherein one of said fiber processing machines is a fiber tuft opener situated downstream of said apparatus as viewed in said conveying direction.

\* \* \* \* \*